United States Patent [19]
Heukensfeldt Jansen et al.

[11] Patent Number: 5,932,878
[45] Date of Patent: *Aug. 3, 1999

[54] REDUCED DEAD TIME RADIATION DETECTION SYSTEM

[75] Inventors: Floribertus Philippus Martinus Heukensfeldt Jansen, Brookfield; Daniel Robert Stafford Taylor, Hartland, both of Wis.

[73] Assignee: General Electric Company, Milwaukee, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/853,769

[22] Filed: May 9, 1997

[51] Int. Cl.$^6$ ...................................... G01T 1/164
[52] U.S. Cl. .................. 250/369; 250/363.1; 250/363.04
[58] Field of Search .................... 250/369, 366, 250/363.07, 363.02, 363.04, 363.1

[56] References Cited

U.S. PATENT DOCUMENTS

| | | | |
|---|---|---|---|
| 4,377,752 | 3/1983 | Sano et al. ............................ | 250/363.1 |
| 5,550,379 | 8/1996 | Schreck et al. ..................... | 250/363.07 |
| 5,689,116 | 11/1997 | Heukensfeldt Jansen ......... | 250/363.07 |

FOREIGN PATENT DOCUMENTS

| | | | |
|---|---|---|---|
| 2633929 | 2/1977 | Germany ........................... | 250/363.07 |
| 2-284088 | 11/1990 | Japan .................................... | 250/369 |

*Primary Examiner*—Constantine Hannaher
*Assistant Examiner*—Darren M. Jiron
*Attorney, Agent, or Firm*—John S. Beulick; Christian G. Cabou; Phyllis Y. Price

[57] ABSTRACT

A nuclear imaging radiation system including a gamma camera which, in one embodiment, includes a scintillation crystal, a collimator and an array of photomultiplier tubes, is described. The collimator is positioned adjacent a face of the crystal, and defines a field of view. The array of photomultiplier tubes is positioned adjacent an opposite face of the crystal, and selected tubes outside the field of view are disabled so that light events outside of the field of view are not processed.

13 Claims, 2 Drawing Sheets

REDUCED DEAD TIME RADIATION DETECTION SYSTEM

FIELD OF THE INVENTION

This invention relates generally to gamma cameras and more particularly, to controlling operation of a large field of view gamma camera when utilizing a small field of view collimator.

BACKGROUND OF THE INVENTION

Gamma cameras typically are used for locating and displaying abnormalities in human glands and organs. More specifically, and with respect to using a gamma camera, gamma-ray-emitting tracer material is administered to a patient, and the tracer material is more greatly absorbed by the abnormality to be detected than by the other tissues. The gamma camera generates data, or an image, representing the distribution of such tracer material within the patient.

A conventional gamma camera includes a collimator and a scintillation crystal, or detector, responsive to radiation stimuli, i.e., gamma rays emitted by the patient. The collimator is positioned adjacent one face of the crystal, and includes a collimator core fabricated from gamma ray attenuating material and having a plurality of openings. An array of photomultiplier tubes typically are positioned adjacent an opposite face of the crystal.

In operation, the gamma rays emitted by the patient are projected toward the collimator core, and those rays projecting through the collimator openings interact with the crystal. The gamma rays impinging upon the collimator septa, i.e., impinging upon the attenuating material and not projecting through the collimator openings, are substantially attenuated and do not interact with the crystal. Particularly, the collimator attenuates, or blocks, certain rays from reaching the crystal. For example, rays which travel at an angular orientation with respect to the collimator openings, i.e., rays which penetrate the collimator septa, may be completely blocked and may not impinge upon the crystal. By blocking these rays, the image quality is improved because such rays generally result in erroneous readings with respect to position and intensity.

Light events occur within the crystal at locations where the rays interact with the crystal lattice structure. The photomultiplier tubes, in response to the light events, produce individual analog outputs. In digital gamma cameras, the analog photomultiplier tube outputs are supplied to analog-to-digital converters (ADCs) which convert the analog outputs to digital signals.

To generate an image, a representation of the distribution of events in the crystal is generated by utilizing a matrix of storage registers whose elements are in one-to-one correspondence with elemental areas of the crystal. The crystal elemental areas are identified by coordinates. Each time a light event occurs in the crystal, the event coordinates are identified and the register in the storage register matrix corresponding to the identified event coordinates is incremented. The contents of a given register in the matrix is a number that represents the number of events that have occurred within a predetermined period of time within an elemental area of the crystal. Such number is directly proportional to the intensity of radiation emitted from an elemental area of the radiation field. The number stored in the register therefore is used to establish the brightness of a display picture element corresponding to the crystal elemental area. The distribution of a radiation field is displayed in terms of the brightness distribution of the display.

Gamma cameras may be used in connection with ultra-high energy isotopes or tracers such as F-18 and FDG. Such high energy isotopes and tracers may generate radiation having an energy value approaching 511 keV. At this energy level, known collimators typically are not effective in preventing unaligned gamma rays from impinging upon the scintillation crystal. Particularly, the higher energy gamma rays are known to penetrate the collimator septa and impinge upon the scintillation crystal, thus reducing image contrast and diagnostic image quality.

To reduce such undesirable collimator penetration caused by high energy isotopes, collimators have been modified to include thicker collimator cores. For example, a lead collimator having a half-value thickness of approximately 6.5 mm is believed to adequately prevent undesirable radiation from penetrating the collimator. Although such thicker collimators reduce gamma ray penetration from high energy isotopes, such thicker collimators also weigh substantially more than typical collimators. With this increased weight, the collimator may exceed the weight bearing capacity of the gamma camera or other nuclear imaging system components such as a collimator cart or exchange system. In addition, changing collimators for different imaging sessions is more cumbersome with heavier collimators.

Rather than utilizing a thicker collimator, reduced field of view collimators may be used to reduce undesired radiation penetration. One such reduced field of view collimator is described, for example, in U.S. patent application Ser. No. 08/853,279 (15-NZ-4480), entitled Gamma Camera Collimator, filed concurrently herewith and assigned to the present assignee. Such reduced field of view collimators are lighter than known collimators, and substantially confine gamma ray penetration to a small portion of the crystal face where imaging will occur. Accordingly, such collimators typically facilitate good imaging without exceeding the weight bearing limitations of nuclear gamma system mechanics, i.e., weight bearing limitations of a system gantry, when utilizing high energy isotopes.

Even with the collimator described above, gamma ray penetration though the collimator may cause a light event outside the desired field of view. Such a light event causes a responsive photomultiplier tube to produce an analog output and contribute to a camera count rate. A high count rate is undesirable in gamma cameras, because such a high count rate degrades image quality. Particularly, the camera electronics are sensitive to count rate, and a high count rate often causes substantial dead time, which is undesirable. In addition, a high count rate may cause an apparent loss of sensitivity since the camera cannot simultaneously record an event within the field of view and elsewhere.

It would be desirable to reduce dead time in gamma camera electronics associated with light events occurring outside of the camera field of view. It also would be desirable to substantially maintain camera sensitivity without significantly reducing image quality.

SUMMARY OF THE INVENTION

These and other objects may be attained by a gamma camera which, in one embodiment, includes at least one disabled, i.e., turned off, photomultiplier tube. Particularly, and in accordance with one embodiment of the present invention, a gamma camera includes a scintillation crystal, a collimator, and an array of photomultiplier tubes. The collimator is positioned adjacent a face of the crystal, and defines a camera field of view. The array of photomultiplier tubes is positioned adjacent an opposite face of the crystal, and at least one of the tubes is disabled, so that it does not transmit a signal in response to a light event. Particularly, photomultiplier tubes that are positioned outside of the field of view are disabled so that light events outside of the field of view do not contribute substantially to an image.

The gamma camera described above reduces dead time in gamma camera electronics associated with light events occurring in the crystal outside of the camera field of view. Such camera also substantially maintains sensitivity without significantly reducing image quality.

DETAILED DESCRIPTION

Figure 1:
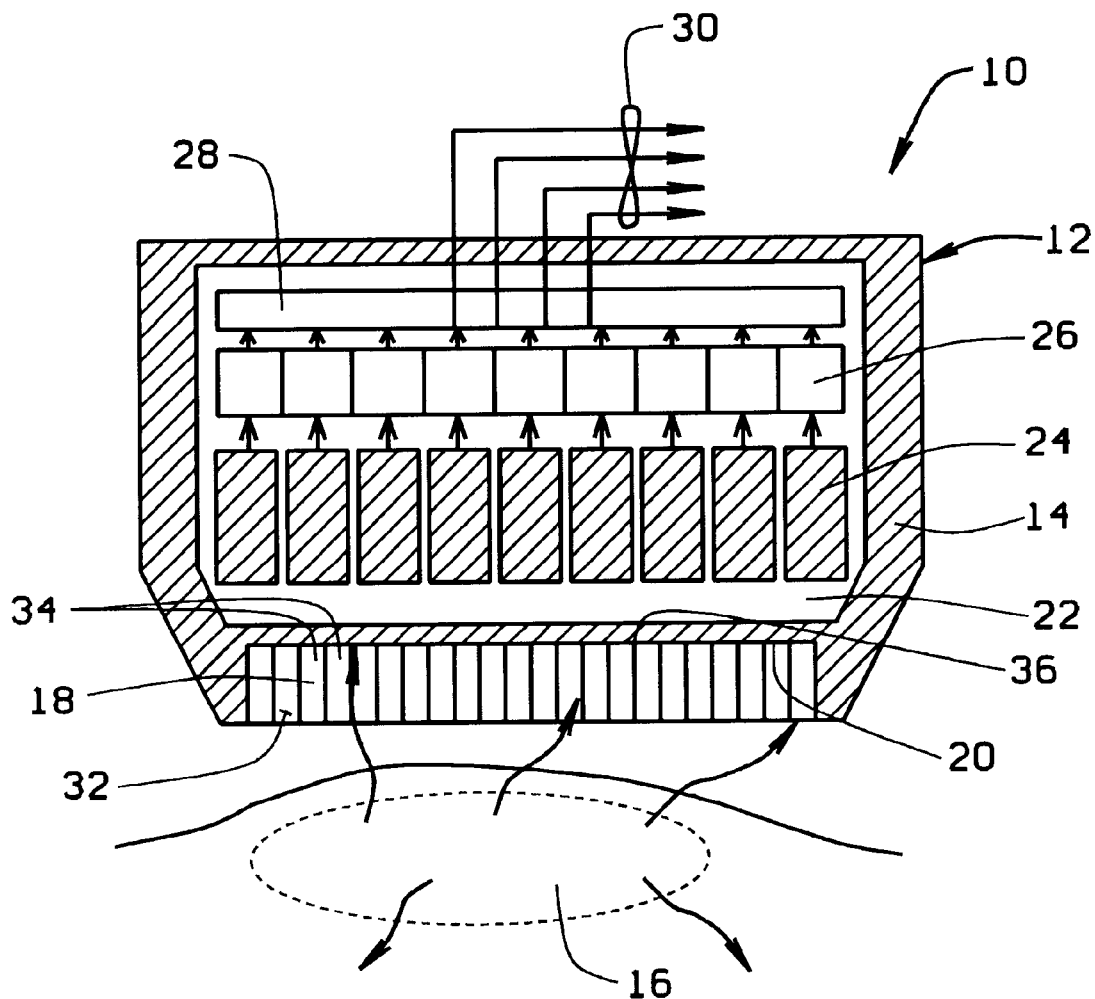
FIG. 1 is a cross-section schematic illustration of a gamma camera.

FIG. 1 is a cross-section schematic illustration of a gamma camera 10 including a detector head 12 having a housing 14 constructed of shielding material, such as lead or steel, for shielding the interior of head 12 from background radiation and from radiation within the patient's body, generally designated at 16, outside the field of view of detector head 12. Detector head 12 further includes a collimator 18 and a scintillation crystal 20. Collimator 18 transfers a gamma ray image of a radioactivity distribution from patient 16 onto scintillation crystal 20. Upon reception of gamma rays, a light event, or incident, occurs, thus causing scintillating crystal 20 to emit one or more light photons. The light photons emitted at the scintillation points in crystal 20 following its absorption of the individual gamma rays pass through a transparent light guide 22 and are shared among a closely-packed array of photomultiplier tubes (PMTs) 24. The total electric charge in the electrical pulses from the output of photomultiplier tubes 24 is proportional to the number of photons received by the photocathode of each photomultiplier tube 24. These pulses contain information on both the energy absorbed within crystal 20 from the gamma rays and the position of the scintillation point, or event. The pulses are then amplified and fed to analog-to-digital converters (ADCs) 26. In one embodiment, the signals from selected tubes 24 may be summed prior to being provided to ADCs 26. ADCs 26 convert the PMT analog outputs to digital signals, which are then processed by circuitry 28. Particularly, camera 10 produces signals on output lines 30 which are transmitted to a processing unit for generating an image for display on, for example, a cathode ray tube. The signals output on lines 30 also typically are stored in the memory of a computer (not shown).

Collimator 18 includes a collimator core 32 which defines a field of view (FOV) of gamma camera 10. Collimator core 32 includes a plurality of plates fabricated from gamma ray attenuating material, and defining a plurality of passages, or openings, 34. Collimator core 32 substantially extends across an entire face 36 of crystal 20.

Collimator 18 generally is provided to prevent rays propagating along an angular path with respect to passages 34 from interacting with crystal 20. By blocking such rays from crystal 20, image quality is believed to be improved because erroneous data which may result from such rays is not generated. Although collimator 18 is sufficiently effective with lower energy isotopes which have been used in the past, such collimator 18 may not sufficiently block, or attenuate, rays generated by higher energy isotopes and tracers. For example, the radioactive tracer FDG emits high energy gamma rays which may penetrate through the collimator plates and impinge upon crystal 20, even if such rays are at an angular orientation with respect to collimator core passages 34 and even if such rays are outside the desired field of view. Therefore, it is possible that in addition to the true data, error data also may be generated.

In addition, light events which occur outside the desire field of view unnecessarily burden camera circuitry 28. For each event the occurs within crystal 20, and even if the event is outside the desired field of view, a dead time is associated with that particular event. Specifically, for each detected event, there is corresponding dead time during which other events are not detected. At high count rates, the dead time can become significant. As the count rate increases, the camera dead time also increases. Accordingly, light events that are outside the desired field of view burden camera circuitry 28 yet provide no true contribution to image generation.

In accordance with one embodiment of the present invention, PMTs which are outside the field of view are disabled. More particularly, PMTs 24 which are outside of the field of view and do not contribute to the image to be generated are disabled, and do not transmit signals to gamma camera circuitry 28 in response to light events in crystal 20. Accordingly, such non-image-contribution light events do not contribute to the camera energy signal, and thus do not cause camera dead time.

The following discussion refers specifically to utilizing a reduced field of view collimator with gamma camera 10. Such reduced field of view collimator has a core of a size less than the field of view of camera 10, and the core defines the area of the reduced field of view. With respect to imaging using high energy isotopes for a portion of a body, such reduced field of view collimator typically provides substantially adequate image quality because high energy isotopes generally are utilized when performing site specific imaging scans such as brain scans or cardiac scans. During such scans, only light events within a reduced portion of crystal face 36 contribute to an image of the brain or heart, respectively. However, it is to be understood that such collimator only is exemplary, and that other collimators may be used.

Figure 2:
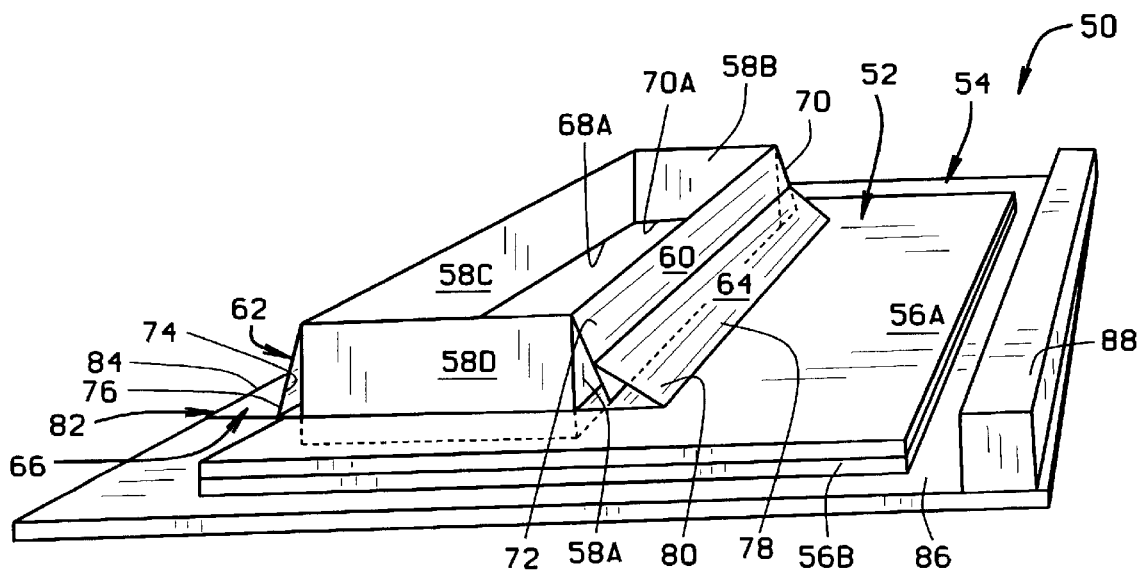
FIG. 2 is a perspective view isometric illustration of a reduced field of view collimator utilized in accordance with one embodiment of the present invention.

An exemplary reduced field of view collimator is described in U.S. patent application Ser. No. 08/853,279 (15-NZ-4480), entitled Gamma Camera Collimator, filed concurrently herewith and assigned to the present assignee. Referring now to FIG. 2, which is a perspective isometric illustration of a reduced field of view collimator 50, such collimator 50 includes an insert 52 secured to a steel support ring 54. Insert 52 includes gamma ray attenuating plates 56A and 56B, core plates 58A, 58B, 58C and 58D, and ramp members 60, 62, 64 and 66. Gamma ray attenuating plate 56A is substantially rectangular and includes an opening 68A having a periphery 70A. Similarly, gamma ray attenuating plate 56B is substantially rectangular and includes an opening 68B having a periphery 70B. Gamma ray attenuating plate 56B is coupled to gamma ray attenuating plate 56A, and openings 68A and 68B in respective attenuating plates 56A and 56B are substantially aligned. Attenuating plates 56A and 56B may be sized, for example, to substantially extend across crystal face 36 (FIG. 1).

Core plates 58A, 58B, 58C and 58D are secured to attenuating plates 56A and 56B at peripheries 70A and 70B of attenuating plate openings 68A and 68B, and extend from attenuating plates 56A and 56B. Core plates 58A, 58B, 58C and 58D define an outer periphery of the collimator core and, as is known in the art, a plurality of collimator plates are positioned in the core to define gamma ray propagation passages through the core.

Ramp member 60 is secured adjacent to core plate 58A, and includes a ramp 70 having a sloped surface 72 extending angularly with respect to attenuating plate 56A and core plate 58A. Similarly, ramp member 62 is secured adjacent core plate 58C, and includes a ramp 74 having a sloped surface 76 extending angularly with respect to attenuating plate 56A and core plate 58C. Ramp member 64 is secured adjacent ramp member 60, and includes a ramp 78 having a sloped surface 80 extending angularly with respect to attenuating plate 56A and sloped surface 72 of ramp member 60. Similarly, ramp member 66 is secured adjacent ramp member 62, and includes a ramp 82 having a sloped surface 84 extending angularly with respect to attenuating plate 56A and sloped surface 76 of ramp member 62.

Insert 52 is secured to support ring 54, and core plates 58A, 58B, 58C and 58D extend through an opening in support ring 54. Particularly, support ring 54 includes a steel plate 86 having an opening, and is coupled to insert 52 so that a periphery of the steel plate opening is substantially aligned with the peripheries 70A and 70B of attenuating plate openings 68A and 68B. Support ring 54 includes a counter balance 88, and counter balance 88 is sized to substantially offset the size and weight of the collimator core and ramps 60, 62, 64 and 66 positioned adjacent the collimator core.

Reduced field of view collimator 50 is positioned adjacent scintillation crystal face 36 and the collimator core extends across a portion of crystal face 36. Attenuating plates 56A and 56B extend across the remaining portion of crystal face 36. Accordingly, gamma rays which are not substantially aligned with the collimator core are substantially prevented from impinging upon scintillation crystal 20. Rather, gamma rays impinging upon attenuating plates 56A and 56B or core plates 58A, 58B, 58C and 58D are substantially blocked, and only the portion of scintillation crystal 20 aligned with the collimator core is substantially impinged upon by radiation.

However, even with reduced field of view collimator 50, it is possible that gamma rays may penetrate collimator 50 and impinge upon scintillation crystal 20 outside the reduced field of view, i.e., impinge upon the portion of scintillation crystal 20 protected by attenuating plate 56. Each radiation penetration outside the reduced field of view, as described above, possibly generates erroneous data, and unnecessarily burdens camera circuitry 28.

Figure 3:
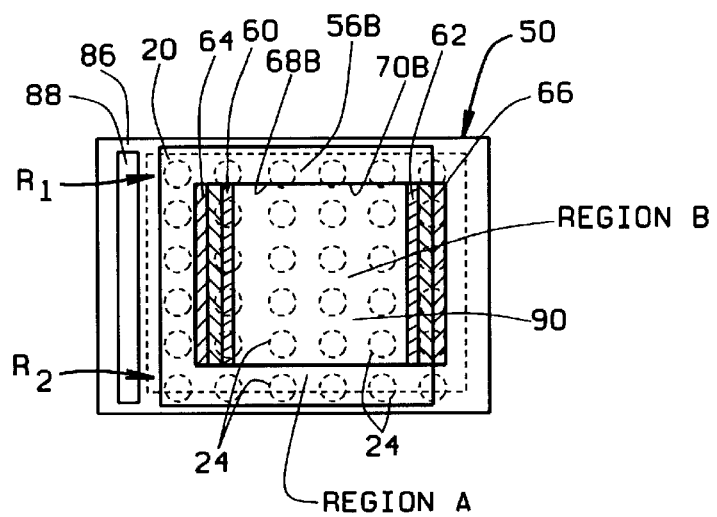
FIG. 3 is a schematic illustration of a gamma camera in accordance with one embodiment of the present invention.

To reduce burden on camera circuitry 28 caused by light events occurring outside the reduced field of view, and in accordance with one embodiment of the present invention, selected PMTs 24 are disabled. For example, FIG. 3 is a schematic illustration of reduced field of view collimator 50 positioned adjacent crystal 20 (dashed lines) and array of PMTs 24. More particularly, crystal 20 is positioned between collimator 50 and PMTs 24. Periphery 70B of attenuating plate opening 68B, as described above, defines a reduced field of view. Particularly, reduced field of view collimator 50 substantially covers crystal 20, except for a portion 90 of crystal 20 substantially aligned with attenuating plate openings 68A and 68B. Accordingly, a plurality of PMTs 24 are positioned within the reduced field of view, i.e., substantially aligned with attenuating plate openings 68A and 68B, and a plurality of PMTs 24 are positioned outside the reduced field of view, i.e., substantially covered by attenuating plates 56A and 56B.

To prevent PMTs 24 from transmitting signals responsive to light events occurring in crystal 20 outside of the reduced field of view, PMTs 24 positioned outside the reduced field of view are disabled. For example, and referring still to FIG. 3, PMTs 24 having their centers positioned in Region A, i.e., outside the reduced field of view and outside periphery 70B are disabled, while PMTs 24 positioned in Region B, i.e., within the reduced field of view and within periphery 70B, are activated. Accordingly, PMTs 24 positioned in Region A do not transmit signals responsive to light events in Region A, and thus light events in Region A do not contribute to the camera energy signal, and thus do not cause camera dead time. In one particular embodiment, it has been found to be beneficial to disable all PMTs 24 outside the field of view except for PMTs 24 around the periphery of the field of view but having their centers outside the field of view.

To disable selected PMTs 24, the gains of such PMTs 24 may be set to approximately about zero. For example a voltage source of such PMT 24 may be turned to a PMT off position. Alternatively, the voltage source of such PMT 24 may be set to a minimal value, i.e., the smallest allowed value for such PMT 24. As yet another alternative, PMTs 24 may be disabled by shutting off respective outputs of amplifiers coupled to such PMTs 24. As still yet another alternative, a reference voltage supplied to respective PMT/amplifiers may be set to a value that minimizes the gain of the PMT/amplifier combination. Still other methods of disabling PMTs are known, and the present invention is not to be limited to the disabling methods discussed above.

Disabling PMTs 24 may possibly impact spatial and energy distortions of camera 10 because such disabled PMTs reduce the field of view over which imaging takes place. Accordingly, and to reduce any such impact, camera 10 may be calibrated after disabling appropriate PMTs 24. Such calibration is neither time consuming nor cumbersome since gamma cameras typically must be recalibrated before imaging with high energy isotopes.

The above-described camera reduces dead time in gamma camera electronics associated with light events occurring in the crystal outside of the camera field of view. Such camera also substantially maintains sensitivity without significantly reducing image quality.

While the above described camera includes a reduced field of view substantially centered within the camera field of view, such reduced field of view may be positioned off-center of the camera field of view. Similarly, while each PMT positioned outside of the reduced field of view was disabled in the above-described camera, fewer PMTs may be disabled. For example, and rather than disabling individual PMTs, entire rows of PMTs may be disabled. Particularly, where the field of view has been reduced by more than one PMT spacing, each row of PMTs positioned outside the reduced field of view may be disabled, (e.g., referring again to FIG. 3, two rows $R_1$ and $R_2$ of array of PMTs 24 may be disabled).

In addition, while the above-described camera included a reduced field of view collimator, other collimators may be used. Particularly, disabling PMTs permits reducing shielding adjacent non-imaging portions of the gamma camera crystal. Accordingly, such camera may be utilized in connection with lighter weight collimators than heretofore acceptable for use with high energy isotopes.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the gamma camera described herein is a digital camera which utilizes PMTs. Many other cameras may be used with other detecting means, e.g., solid state devices, could be used. Similarly, while the collimator described herein was a reduced field of view collimator, other collimators may be used. Accordingly, the spirit and scope of the invention are to be limited only by the terms of the appended claims.

We claim:

1. A nuclear radiation imaging system for imaging an object of interest, said system comprising a gamma camera and a high-energy collimator defining a field of view, said collimator comprising a gamma ray attenuating plate having an opening therein, at least one core plate extending from said attenuating plate at a periphery of said attenuating plate opening, and at least one ramp member secured to said one core plate, said one ramp member comprising a ramp having a sloped surface extending angularly with respect to said attenuating plate and said core plate, and wherein said gamma camera comprising an array of photomultiplier tubes with at least one of said photomultiplier tubes positioned within said field of view and at least one of said photomultiplier tubes outside of said field of view disabled.

2. A nuclear radiation system in accordance with claim 1 wherein said array of photomultiplier tubes comprises a plurality of rows of photomultiplier tubes, at least one row of said array is positioned outside of said field of view, and wherein each photomultiplier tube in said row positioned outside of said field of view is disabled.

3. A nuclear radiation system in accordance with claim 1 wherein the gain of said disabled photomultiplier tube is approximately about zero.

4. A nuclear radiation system in accordance with claim 1 wherein said gamma camera further comprises a plurality of amplifiers, each amplifier coupled to one of said photomultiplier tubes, and wherein said output of said amplifier coupled to said disabled tube is approximately about zero.

5. A gamma camera comprising an array of photomultiplier tubes and a high-energy collimator defining a field of view, said collimator comprising a gamma ray attenuating plate having an opening therein, at least one core plate extending from said attenuating plate at a periphery of said attenuating plate opening, and at least one ramp member secured to said one core plate, said one ramp member comprising a ramp having a sloped surface extending angularly with respect to said attenuating plate and said core plate, at least one of said photomultiplier tubes outside of said field of view disabled.

6. A gamma camera in accordance with claim 5 wherein said array of photomultiplier tubes comprises a plurality of rows of photomultiplier tubes, at least one row of said array is positioned outside of said field of view, and wherein each photomultiplier tube in said row positioned outside of said field of view is disabled.

7. A gamma camera in accordance with claim 5 wherein the gain of said disabled photomultiplier tube is approximately about zero.

8. A gamma camera in accordance with claim 5 further comprising a plurality of amplifiers, each amplifier coupled to one of said photomultiplier tubes, and wherein said output of said amplifier coupled to said disabled tube is approximately about zero.

9. A method for reducing dead time in a gamma camera, the gamma camera including a collimator, a scintillation crystal, and an array of photomultiplier tubes, the array of photomultiplier tubes including at least one row of photomultiplier tubes, the collimator including a gamma ray attenuating plate having an opening therein, at least one core plate extending from the attenuating plate at a periphery of the attenuating plate opening and at least one ramp member secured to the one core plate, the one ramp member comprising a ramp having a sloped surface extending angularly with respect to the attenuating plate and the core plate, the collimator defining a field of view, said method comprising:

identifying at least one photomultiplier tube positioned outside of the field of view; and disabling the identified photomultiplier tube.

10. A method in accordance with claim 9 further comprising the step of disabling each photomultiplier tube positioned outside of the field of view.

11. A method in accordance with claim 9 wherein the array of photomultiplier tubes includes a plurality of rows of photomultiplier tubes, and wherein disabling at least one photomultiplier tube comprises the step of disabling at least one row of photomultiplier tubes.

12. A method in accordance with claim 9 wherein disabling the photomultiplier tube comprises the step of setting the gain of the photomultiplier tube to approximately about zero.

13. A method in accordance with claim 9 wherein the gamma camera further includes a plurality of amplifiers, each amplifier coupled to one of said photomultiplier tubes, and wherein disabling at least one photomultiplier tube comprises the step of substantially setting the output of the amplifier associated with the identified photomultiplier tube to approximately about zero.

* * * * *